(12) United States Patent
Weiss et al.

(10) Patent No.: US 12,359,220 B2
(45) Date of Patent: Jul. 15, 2025

(54) GUIDED MAGNETIC NANOSTRUCTURES FOR TARGETED AND HIGH-THROUGHPUT INTRACELLULAR DELIVERY

(71) Applicant: THE REGENTS OF THE UNIVERSITY OF CALIFORNIA, Oakland, CA (US)

(72) Inventors: Paul S. Weiss, Los Angeles, CA (US); Hsian-Rong Tseng, Los Angeles, CA (US); Xiaobin Xu, Los Angeles, CA (US); Natcha Wattanatorn, Los Angeles, CA (US); Qing Yang, Los Angeles, CA (US); Steven J. Jonas, Hawthorne, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1201 days.

(21) Appl. No.: 16/962,509

(22) PCT Filed: Jan. 29, 2019

(86) PCT No.: PCT/US2019/015650
§ 371 (c)(1),
(2) Date: Jul. 15, 2020

(87) PCT Pub. No.: WO2019/148184
PCT Pub. Date: Aug. 1, 2019

(65) Prior Publication Data
US 2020/0347409 A1 Nov. 5, 2020

Related U.S. Application Data

(60) Provisional application No. 62/623,449, filed on Jan. 29, 2018.

(51) Int. Cl.
*C12N 15/87* (2006.01)
*G01N 33/543* (2006.01)

(52) U.S. Cl.
CPC ....... *C12N 15/87* (2013.01); *G01N 33/54326* (2013.01); *C12N 2310/141* (2013.01)

(58) Field of Classification Search
CPC .......................... C12N 15/87; G01N 33/54326
See application file for complete search history.

(56) References Cited

U.S. PATENT DOCUMENTS

| | | |
|---|---|---|
| 5,457,041 A | 10/1995 | Ginaven et al. |
| 6,231,496 B1 * | 5/2001 | Wilk ........ A61N 2/06 128/898 |
| 6,611,707 B1 | 8/2003 | Prausnitz et al. |
| 8,162,901 B2 | 4/2012 | Gonnelli et al. |
| 9,394,547 B2 | 7/2016 | Chen et al. |
| 2006/0105170 A1 * | 5/2006 | Dobson ........ H01F 1/24 252/62.51 R |
| 2010/0081130 A1 * | 4/2010 | Lee ........ A61K 49/1848 435/6.16 |
| 2011/0168968 A1 | 7/2011 | Yang et al. |
| 2012/0276573 A1 | 11/2012 | VanDersarl et al. |
| 2013/0011441 A1 | 1/2013 | Hollinger et al. |
| 2013/0165772 A1 | 6/2013 | Traverso et al. |
| 2014/0045179 A1 | 2/2014 | Wang et al. |
| 2015/0283265 A1 * | 10/2015 | Peyman ........ A61K 38/465 424/491 |

FOREIGN PATENT DOCUMENTS

| | | |
|---|---|---|
| WO | 2006/116065 | 11/2006 |
| WO | WO 2010/076337 | * 7/2010 |
| WO | WO 2010/076337 A1 | 7/2010 |
| WO | WO 2013059343 | 4/2013 |
| WO | WO 2015/089427 | 6/2015 |
| WO | 2016/069752 | 5/2016 |
| WO | WO 2017/011320 | 1/2017 |

OTHER PUBLICATIONS

Qiu et al. (Nature Communications, 8, 15594, 2017) (Year: 2017).*
Li, J., et al., "Nanoconfined Atomic Layer Deposition of TiO2/Pt Nanotubes: Toward Ultrasmall Highly Efficient Catalytic Nanorockets". Adv. Funct. Mater. 2017, 27, 1700598.
Xu, X., et al. "Near-Field Enhanced Plasmonic-Magnetic Bifunctional Nanotubes for Single Cell Bioanalysis", Adv. Funct. Mater. 2013, 23, 4332-4338.
Xu, H., et al., "Sperm-hybrid micromotor for drug delivery in the female reproductive tract", ACS Nano, dated Mar. 24, 2017.
Pelaz, B., et al. "Diverse Applications of Nanomedicine". ACS Nano 2017, 11, 2313-2381.
Hulteen, J. C., et al. "Nanosphere Lithography: A Materials General Fabrication Process for Periodic Particle Array Surfaces". J. Vac. Sci. Technol. A 1995, 13, 1553-1558.

(Continued)

*Primary Examiner* — Genevieve S Alley
(74) *Attorney, Agent, or Firm* — VISTA IP LAW GROUP LLP

(57) ABSTRACT

A method of transporting biomolecular cargo intracellularly into cells includes the operations of providing magnetic nanostructures (e.g., nanospears, nanostars, nanorods, and other nanometer-sized structures) carrying the biomolecular cargo thereon and applying an external magnetic field to move the magnetic nanostructures into physical contact with at least some of the cells (or the cells into the magnetic nanostructures). The magnetic nanostructures move into physical contact with a single cell, a subset of cells, or all cells. The external magnetic field may be applied by a moving permanent magnet although an electromagnetic may also be used. The biomolecular cargo may include a molecule, a plurality of molecules, or higher order biological constructs. For example, the biological construct may include DNA plasmids, small interfering RNA, proteins, or targeted nuclease gene-editing cargo such as zinc-finger nucleases, transcription activator-like effector nucleases, Cas9 protein, Cas9 mRNA, and associated guide RNA sequences.

9 Claims, 11 Drawing Sheets

(56) References Cited

OTHER PUBLICATIONS

Wang, X. D., et al. "Large-Scale Fabrication of Ordered Nanobowl Arrays", Nano Lett. 2004, 4, 2223-2226.
Gao, P. Q.;, et al. "Large-Area Nanosphere Self-Assembly by a Micro-Propulsive Injection Method for High Throughput Periodic Surface Nanotexturing". Nano Lett. 2015, 15, 4591-4598.
Zhang, L.; et al. "A Nanomesh Scaffold for Supramolecular Nanowire Optoelectronic Devices". Nat. Nanotechnol. 2016, 11, 900-906.
Xu, X.; et al. "Ordered Arrays of Raman Nanosensors for Ultrasensitive and Location Predictable Biochemical Detection". Adv. Mater. 2012, 24, 5457-5463.
Richardson, J. J.; et al. "Technology-Driven Layer-by-Layer Assembly of Nanofilms". Science 2015, 348, aaa2491.
Chiappini, C.; et al. "Biodegradable Silicon Nanoneedles Delivering Nucleic Acids Intracellularly Induce Localized in Vivo neovascularization". Nat. Mater. 2015, 14, 532-539.
Esteban-Fernández de Ávila, B., et al. "Nanomotor-Enabled Ph-Responsive Intracellular Delivery of Caspase-3: Toward Rapid Cell Apoptosis". ACS Nano 2017, 11, 5367-5374.
García-López, V. et al. "Molecular Machines Open Cell Membranes", Nature 2017, 548, 567-572.
Golshadi, M., et al., "Carbon nanotube arrays for intracellular Delivery and biological applications", RIT Scholar Works, Aug. 2016.
Guo, J. et al. "Electric-Field Guided Precision Manipulation of Catalytic Nanomotors for Cargo Delivery and Powering Nanoelectromechanical Devices" ACS Nano 2018.
Hou, S. et al., "Supramolecular Nanosubstrate-Mediated Delivery for Reprogramming and Transdifferentiation of Mammalian Cells" Small 2015, 11, 2499-2504.
Kim, K. et al. "Micromotors with Step-Motor Characteristics by Controlled Magnetic Interactions among Assembled Components" ACS Nano 2015, 9, 548-554.
Kollmannsperger, A., et al. "Live-Cell Protein Labelling with Nanometre Precision by Cell Squeezing". Nat. Commun. 2016, 7, 10372.
Lee, J. et al., "Nonendocytic Delivery of Functional Engineered Nanoparticles into the Cytoplasm of Live Cells Using a Novel, High-Throughput Microfluidic Device" Nano Lett. 2012, 12, 6322-6327.
Li, J. et al. "Micro/Nanorobots for Biomedicine: Delivery, Surgery, Sensing, and Detoxification". Science Robotics 2017, 2, eaam6431.
Li, T. et al., "Highly Efficient Freestyle Magnetic Nanoswimmer", Nano Lett. 2017, 17, 5092-5098.
Paxton, W. F. et al., "Catalytic Nanomotors: Autonomous Movement of Striped Nanorods" J. Am. Chem. Soc. 2004, 126, 13424-13431.
Peng, J. et al., "Molecular Recognition Enables Nanosubstrate-Mediated Delivery of Gene-Encapsulated Nanoparticles with High Efficiency". ACS Nano 2014, 8, 4621-4629.
Ren, L. et al., "Rheotaxis of Bimetallic Micromotors Driven by Chemical-Acoustic Hybrid Power", ACS Nano 2017, 11, 10591-10598.
Shalek, A., et al. "Vertical silicon nanowires as a universal platform for delivering biomolecules into living cells," 1870-1875, PNAS, Feb. 2, 2010, vol. 107, No. 5.
Sharei, A., et al., "A vector-free microfluidic platform for intracellular delivery," 2082-2087, PNAS, Feb. 5, 2013, vol. 110, No. 6.
Stewart, M. P., et al. "In Vitro and Ex Vivo Strategies for Intracellular Delivery" Nature 2016, 538, 183-192.
Ding, X. et al. "High-Throughput Nuclear Delivery and Rapid Expression of DNA via Mechanical and Electrical Cell-Membrane Disruption", Nat. Biomed. Eng. 2017, 1, 0039.
Wang, S., et al. "Highly Efficient Capture of Circulating Tumor Cells by Using Nanostructured Silicon Substrates with Integrated Chaotic Micromixers" Angew. Chem. Int. Ed. 2011, 50, 3084-3088.

Whitehead, K. A., et al. "Knocking Down Barriers: Advances in siRNA Delivery", Nat. Rev. Drug Discov. 2009, 8, 129-138.
Xu, L. et al. "Light-Driven Micro/Nanomotors: From Fundamentals to Applications", Chem. Soc. Rev. 2017.
Yin, H. et al., "Therapeutic genome editing by combined viral and non-viral delivery of CRISPR system components in vivo," Nat Biotechnol. Mar. 2016 ; 34(3): 328-333.
Yoo, S. M., et al. "Electrotriggered, Spatioselective, Quantitative Gene Delivery into a Single Cell Nucleus by Au Nanowire Nanoinjector," Nano Lett. 2013, 13, 2431-2435.
Baraban, L., et al. "Catalytic Janus Motors on Microfluidic Chip: Deterministic Motion for Targeted Cargo Delivery". ACS Nano 2012, 6, 3383-3389.
Bruckbauer, A, et al., "Writing with DNA and Protein Using a Nanopipet for Controlled Delivery", J. Am. Chem. Soc. 2002, 124, 8810-8811.
Bucaro, M. A., et al. "Fine-Tuning the Degree of Stem Cell Polarization and Alignment on Ordered Arrays of High-Aspect-Ratio Nanopillars". ACS Nano 2012, 6, 6222-6230.
Chiappini, C., et al. "Biodegradable Nanoneedles for Localized Delivery of Nanoparticles in Vivo:Exploring the Biointerface". ACS Nano 2015, 9, 5500-5509.
Elbakry, A, et al. "Layer-by-Layer Assembled Gold Nanoparticles for Sirna Delivery" Nano Lett. 2009, 9, 2059-2064.
Esteban-Fernández de Ávila, B., et al. "Acoustically Propelled Nanomotors for Intracellular Sirna Delivery". ACS Nano 2016, 10, 4997-5005.
Fan, D., et al. "Subcellular-Resolution Delivery of a Cytokine through Precisely Manipulated Nanowires". Nat. Nanotechnol. 2010, 5, 545-551.
Kim, K., et al. "Ultrahigh-Speed Rotating Nanoelectromechanical System Devices Assembled from Nanoscale Building Blocks", Nat. Commun. 2014, 5, 3632.
Wen, R., et al., "Intracellular Delivery and Sensing System Based on Electroplated Conductive Nanostraw Arrays," DOI: 10.1021 ACS Appl. Mater. Interfaces 2019, 11, 43936-43948.
Xu, X., et al., "Multiple-Patterning Nanosphere Lithography for Fabricating Periodic Three-Dimensional Hierarchical Nanostructures" ACS Nano 2017, 11, 10384-10391.
Zhang, F., et al. "Hierarchical Nanowire Arrays as Three-Dimensional Fractal Nanobiointerfaces for High Efficient Capture of Cancer Cells". Nano Lett. 2015, 16, 766-772.
Xie, X., et al. "Nanostraw-Electroporation System for Highly Efficient Intracellular Delivery and Transfection", ACS Nano 2013, 7, 4351-4358.
Zhu, F., et al., "Sub-Cellular Resolution Delivery of a Cytokine via Precisely Manipulated Nanowires," Article in Nature Nanotechnology Jul. 2010.
The extended European search report dated Feb. 26, 2021 for the European Patent Application No. 19743640.5-1118 (8 pages).
Dong Cai et al., Highly efficient molecular delivery into mammalian cells using carbon nanotube spearing, Nature Methods, vol. 2, No. 6, 449-454 (Jun. 2005).
Xiaobin Xu et al., Precision-Guided Nanospears for Targeted and High-Throughput Intracellular Gene Delivery, ACS Nano, 12, 4503-4511 (2018).
Communication pursuant to Rules 70(2) and 70a(2) EPC dated Mar. 16, 2021 for the European Patent Application No. 19743640.5-1118 (1 page).
PCT International Search Report for PCT/US2019/015650, Applicant: The Regents of the University of California, Form PCT/ISA/210 and 220, dated Apr. 18, 2019 (3pages).
PCT Written Opinion of the International Search Authority for PCT/US2019/015650, Applicant: The Regents of the University of California, Form PCT/ISA/237, dated Apr. 18, 2019 (6pages).

* cited by examiner

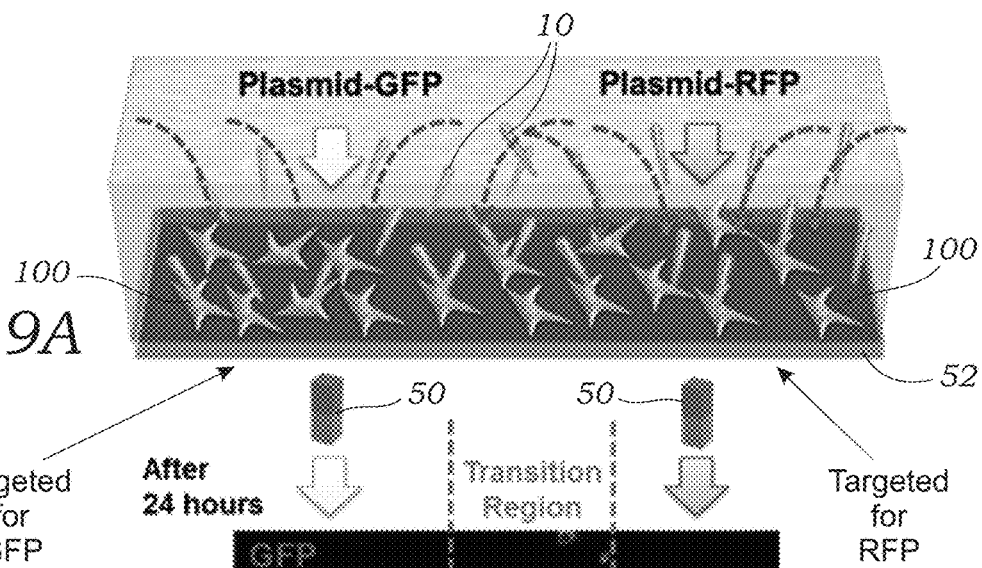
FIG. 9A
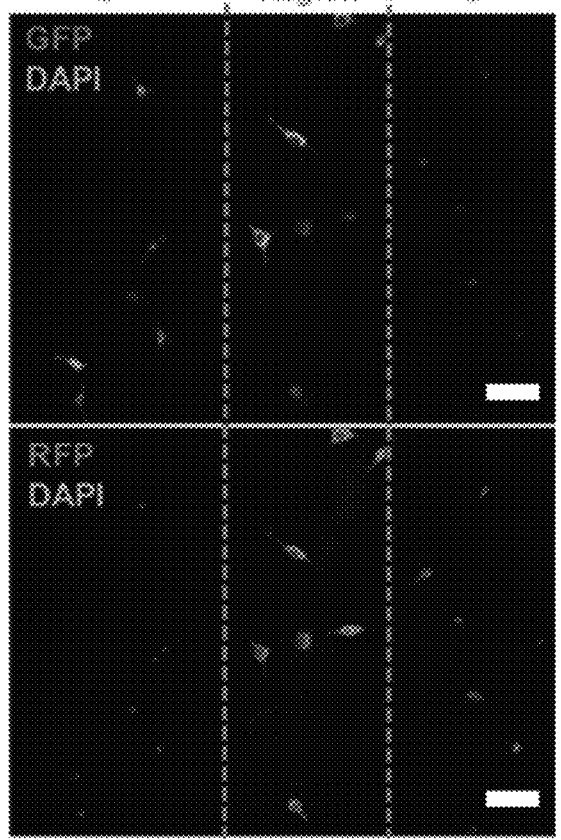
FIG. 9B
FIG. 9C
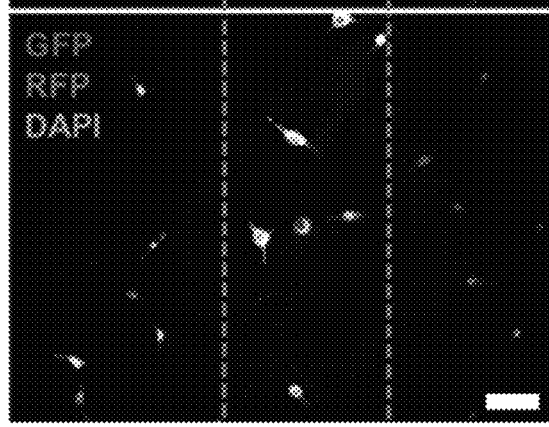
FIG. 9D

GUIDED MAGNETIC NANOSTRUCTURES FOR TARGETED AND HIGH-THROUGHPUT INTRACELLULAR DELIVERY

RELATED APPLICATION

This Application is a U.S. National Stage filing under 35 U.S.C. § 371 of International Application No. PCT/US2019/015650, filed Jan. 29, 2019, which claims priority to U.S. Provisional Patent Application No. 62/623,449 filed on Jan. 29, 2018, which are hereby incorporated by reference. Priority is claimed pursuant to 35 U.S.C. §§ 119, 371 and any other applicable statute.

STATEMENT REGARDING FEDERALLY SPONSORED RESEARCH AND DEVELOPMENT

This invention was made with government support under Grant Number CA198900, awarded by the National Institutes of Health, and Grant Number 1636136, awarded by the National Science Foundation. The government has certain rights in the invention.

TECHNICAL FIELD

The technical field generally relates to the use of small, magnetic nanostructures that are used to carry and/or deliver biomolecular cargo intracellularly to cells.

BACKGROUND

High-throughput and targeted intracellular delivery of biomolecules is critical for applications in cell and molecular biology and emerging clinical applications that make use of gene-editing systems. Existing approaches that use viruses, external electric fields, or harsh chemical reagents are either costly, apply undesirable stresses or toxicities to the cells, or are inefficient. Improving the safety, speed, cost effectiveness, and efficiency of intracellular delivery methods remains a long-standing challenge. Currently, membrane-disruption-based approaches are attractive candidates for universal delivery systems in vitro and ex vivo, including electroporation, squeezing, fluid shear, direct microinjection, photothermal, sharp nanostructures, and combinations of these techniques. In particular, configurations of needle-like nanostructures can physically penetrate flexible cell membranes to deliver biomolecules to cells efficiently and, if desired, in parallel with minimal impact on viability and metabolism due to their nanoscale sharp tips. So far, most reported nano-needle platforms are comprised of arrays grown on planar substrates that support the growth of adherent cells and gently pierce cellular membranes to enable transfection. However, difficulties with releasing the modified cells from these nanostructured substrates and collecting them for further study has precluded wider application of nanosubstrate-mediated delivery.

Recently, substantial progress has been made in the development of nano-/micromotor systems, which can be internally or externally powered to move in liquid environments. These functional nanomaterials have been applied in several diverse biomedical applications, including biosensing, biomolecule delivery, and nanosurgery. In particular, the capability for guidance and versatile cargo integration of the nano/micromotors have enabled the active transport and delivery of therapeutic payloads. Thus far, these nanosystems have limited precision in terms of their guidance and biocompatibility due to byproducts from catalytic reactions that propel the nano-/micromotor structures to their targets.

SUMMARY

In one embodiment, the invention relates to the design and fabrication of magnetic nanostructures that can be configured readily for single-cell modification and that can also be scaled progressively for direct and highly efficient intracellular delivery of biomolecular cargo. These biocompatible nanomaterials can be guided precisely to target cells without the need for chemical propellants by manipulation of locally applied magnetic fields. This technique offers several advantages over conventional non-viral transfection approaches, and is suitable for both molecular cell biology studies and translational medicine.

In one embodiment, a method of transporting biomolecular cargo intracellularly into cells includes the operations of providing one or more magnetic nanostructures (e.g., nanospears, nanostars, and other nanometer-sized structures) carrying the biomolecular cargo thereon and applying an external magnetic field to move the magnetic nanostructures into physical contact with at least some of the cells. The magnetic nanostructures move into physical contact with a single cell, a subset of cells (e.g., cells of a particular type or phenotype), or all cells. In some embodiments, the particular cell or multiple cells are targeted by the magnetic nanostructures. This targeting may be accomplished by the positioning and/or manipulation of an external magnetic field on the magnetic nanostructures. In one embodiment, the one or more magnetic nanostructures include a plurality of or many magnetic nanostructures. The external magnetic field may be applied by a moving permanent magnet although an electromagnetic may also be used as an alternative to a permanent magnet. The biomolecular cargo may include a molecule, a plurality of molecules, or higher order biological constructs. For example, the biological construct may include DNA plasmids, small interfering RNA, proteins, or targeted nuclease gene-editing cargo such as zinc-finger nucleases, transcription activator-like effector nucleases, Cas9 protein, Cas9 mRNA, and associated guide RNA sequences. In a preferred embodiment, the magnetic nanostructures have at least one sharp end, tip, or surface. That is to say at least a portion of the magnetic nanostructure has a tip or end that is sharp or pointed to aid in or facilitate penetration into the cellular membrane or wall of the cell.

In another embodiment, a method of transporting biomolecular cargo intracellularly into cells includes providing one or more magnetic nanostructures carrying the biomolecular cargo thereon. An external magnetic field is then applied, in some embodiments, to orient the magnetic nanostructures into a particular orientation. The one or more cells and/or the magnetic nanostructures are then moved so as to physically contact one another. In some embodiments, there is no need for the magnetic nanostructures to be oriented in a particular orientation prior to movement. For example, magnetic nanostars do not need to be oriented given their three-dimensional structure. In some embodiments, the one or more cells may be moved toward the magnetic nanostructures which are stationary. Alternatively, the magnetic nanostructures may be moved toward the one or more cells which are stationary (e.g., they may be adhered on a substrate or other surface). In yet another alternative, the one or more cells and the magnetic nanostructures are moved toward one another.

In another embodiment, an intracellular delivery vehicle includes one or more magnetic nanostructures having at least one sharp end, tip, or surface, the magnetic nanostructures being formed of a substrate material having a magnetic coating formed thereon and biomolecular cargo bound to or otherwise adhered to the magnetic nanostructures. The biomolecular cargo may be electrostatically bound to one or more surface layers. The biomolecular cargo may also be covalently bound to a linker molecule (or multiple linker molecules) formed on the magnetic nanostructures or directly to the surface. In one embodiment, a coating of an inert noble metal or metal oxide is formed on the coating. This inner coating may further be coated with one or more layers which can be used carry the biomolecular cargo. For example, the inert noble metal may be coated with a self-assembled monolayer (SAM) formed thereon and an overlying anchoring layer.

The magnetic nanostructures may include any number of shapes and configurations. This includes, by way of example, nanospears, nanostars, nanorods, particles having protuberances thereon. Magnetic nanostructures may be largely two-dimensional or they may be three-dimensional structures. The magnetic nanostructures may require orientation prior to making contact with the cell(s) of interest in some embodiments. In other embodiments, the magnetic nanostructures do not require orientation prior to contact with the cell(s) of interest.

BRIEF DESCRIPTION OF THE DRAWINGS

FIG. 9A schematically illustrates how specific cells contained in a targeted large area are transfected by manipulation of multiple nanospears carrying green fluorescent protein (GFP) and red fluorescent protein (RFP) respectively. Cells on the left of the area are targeted with GFP while cells on the right of the area are targeted with RFP. Note that 4',6-diamidino-2-2phenylindole (DAPI) is used to stained the nucleus of all the living and dead cells. Green: GFP; Blue: DAPI. Red: RFP. Scale bars: 50 μm.

FIG. 9B illustrates a fluorescence microscopy image after 24 h of the cells on the substrate stained with GFP and DAPI. The GFP stained cells are located on the left side of the substrate.

FIG. 9C illustrate a fluorescence microscopy image after 24 h of the cells on the substrate stained with RFP and DAPI. The RFP stained cells are located on the right side of the substrate.

FIG. 9D illustrates the overlaid images of FIGS. 9B and 9C.

DETAILED DESCRIPTION OF THE ILLUSTRATED EMBODIMENTS

Figure 1A:
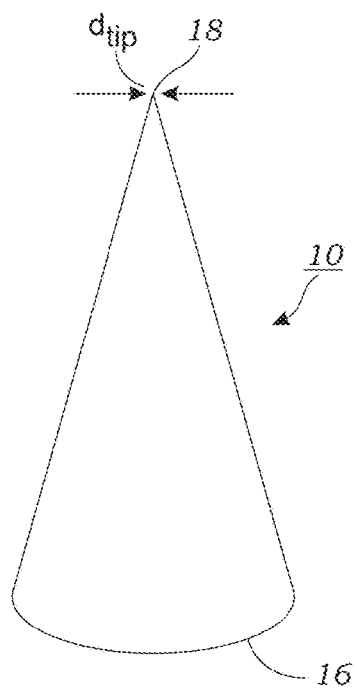
FIG. 1A illustrates an embodiment of a magnetic nanostructure in the form of a nanospear.

In one embodiment, magnetic nanostructures 10 such as those illustrated in FIGS. 1A-1D are disclosed that are designed to carry biomolecular cargo 14 thereon. In some embodiments as described herein, the magnetic nanostructures 10 include one or more biocompatible surface layers 12 such as illustrated in FIG. 2 that is configured to aid in the attachment of biomolecular cargo 14 to the magnetic nanostructures 10. In one exemplary embodiment, the biocompatible surface layer 12 includes a gold layer that has a self-assembled monolayer (SAM) formed thereon and an overlying anchoring layer 46.

Figure 2:
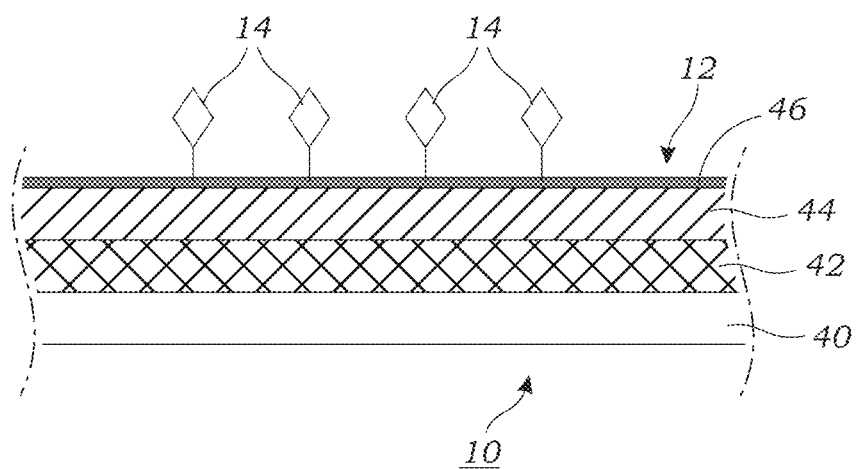
FIG. 2 illustrates a cross-sectional view illustrating various layers of the magnetic nanostructure according to one embodiment.
Figure 5A:
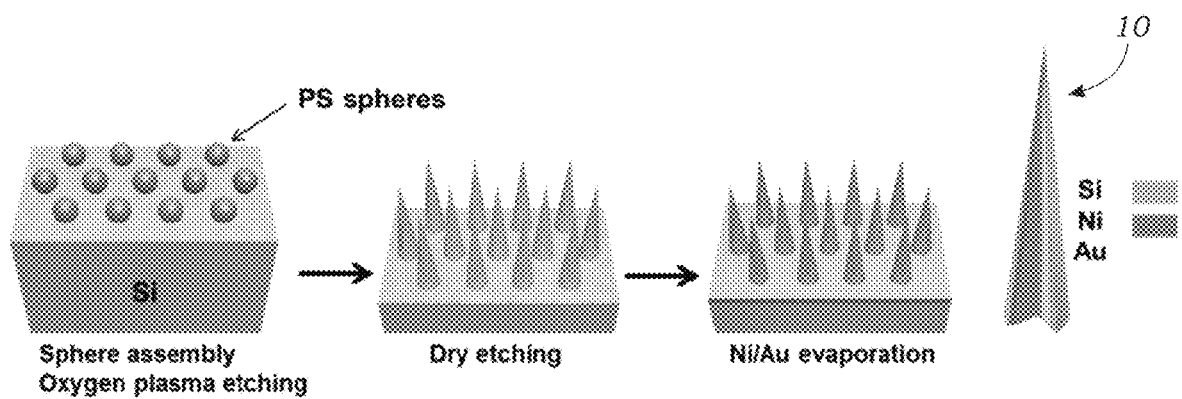
FIG. 5A schematically illustrates the fabrication of magnetic nanospear arrays. Polystyrene (PS) nanospheres are first assembled on a silicon (Si) wafer followed by size reduction via oxygen plasma etching. Dry etching is then applied to etch the Si and nanospheres simultaneously to generate Si nanospear arrays. Next, layers of nickel (Ni, 40 nm) and gold (Au, 10 nm) are evaporated on the Si nanospear arrays
Figures 5B, 5C:
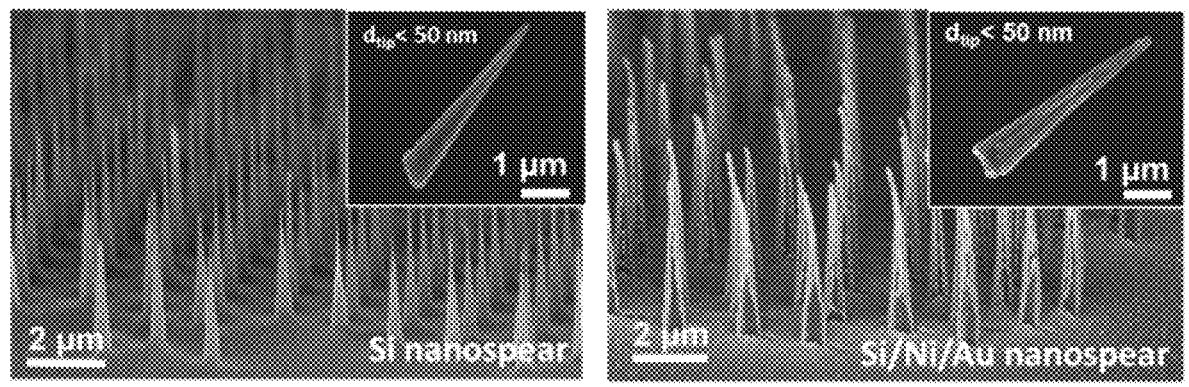
FIG. 5B illustrates scanning electron microscopy (SEM) images of ordered silicon nanospear arrays (prior to coating). Inset image is an individual Si nanospear.
FIG. 5C illustrates SEM images of ordered silicon nanospear arrays (after coating with nickel and gold). Inset image is an individual Si/Ni/Au nanospears.

The magnetic nanostructures 10 may include magnetic nanospears 10 such as that illustrated in FIG. 1A. Magnetic nanospears 10 generally have a conical shape with a base portion 16 that terminates at a tip or end 18 that is sharp or pointed as illustrated in FIG. 1A. The base portion 16 may, in some embodiments, have a circular shape although other cross-sectional shapes are contemplated. The height of the nanospear (e.g., the longest dimension) is typically larger than the width or diameter of the base portion 16 and may fall within the range of about several microns or longer. For example, in one particular example, the magnetic nanospear 10 may have a length of several microns (e.g., 5 μm in length) with a tip diameter ($d_{tip}$) at the sharp tip of less than 50 nm. The base portion 16 may have a width or diameter that is several hundred nanometers or larger (e.g., micrometer sized). For instance, as seen in FIGS. 5B and 5C the base of the magnetic nanospear 10 is at around or under 1 μm.

Figure 1B:
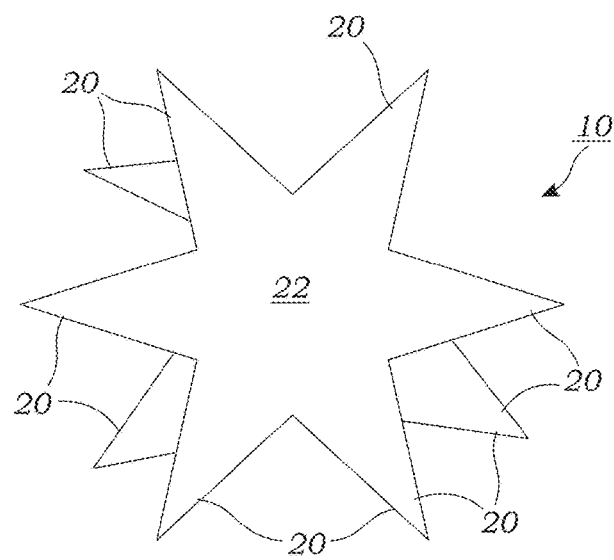
FIG. 1B illustrates an embodiment of a magnetic nanostructure in the form of a nanostar.

FIG. 1B illustrates another embodiment of a magnetic nanostructure 10 in the form of a magnetic nanostar 10. The magnetic nanostar 10 structure includes a plurality of radiating projections 20 that extend outward from a core or center portion 22. Some or all of the radiating projections 20 have a sharp tip or end as illustrated in FIG. 1B. The radiation projections 20 typically radiate in multiple directions making the magnetic nanostar 10 structure three-dimensional. Nanostar structures may be formed by the seed-mediated growth of branched gold nanoparticles. Details regarding seed-mediated growth of these structures may be found in Barbosa et al., Tuning Size and Sensing Properties in Colloidal Gold Nanostars, Langmuir, 2010, 26 (18), pp 14943-14950, which is incorporated by reference. Techniques and methods for creating magnetic gold nanostars may be found in Minati et al., One-step synthesis of magnetic gold nanostars for bioimaging applications, RSC Adv., 2015, 5, 103343-103349, which is incorporated by reference.

Figure 1C:
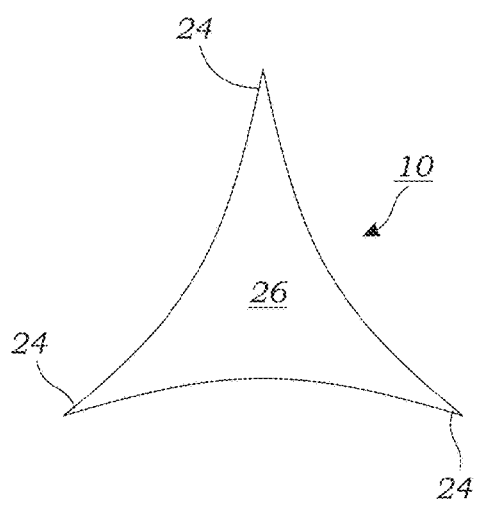
FIG. 1C illustrates an embodiment of a magnetic nanostructure in the form of a triangle.

FIG. 1C illustrates another embodiment of a magnetic nanostructure 10. In this embodiment, the magnetic nanostructure 10 is the form of a magnetic triangle 10 with three tips or ends 24 that extend from a core or center portion 26 and are sharp or pointed. In this particular embodiment, the magnetic triangle 10 with its sharp tips or ends 24 generally lies in a plane making this magnetic nanostructure 10 having a two-dimensional profile (even though there is some thickness to the triangle). Nanosphere lithography may be used in the formation of magnetic triangles 10. For example, two-dimensional ordered arrays of gold triangular shaped particles may be made using nanosphere lithography techniques such as those disclosed in Tan et al., Fabrication of Size-Tunable Gold Nanoparticles Array with Nanosphere Lithography, Reactive Ion Etching, and Thermal Annealing, J. Phys. Chem. B, 2005, 109 (22), pp. 11100-11109, which is incorporated herein by reference.

Figure 1D:
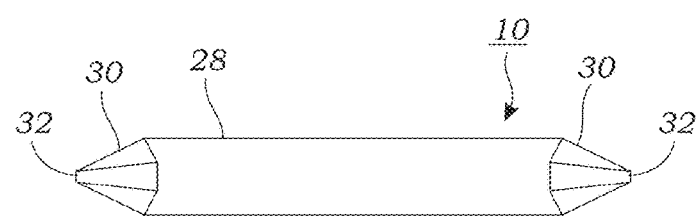
FIG. 1D illustrates an embodiment of a magnetic nanostructure in the form of a nanorod.

FIG. 1D illustrates yet another embodiment of an exemplary magnetic nanostructure 10. In this embodiment, the magnetic nanostructure 10 is in the form of a magnetic nanorod 10. The magnetic nanorod 10 has a central portion 28 and two end portions 30 that may include faceted ends that terminate at a sharp end or tip 32. Details regarding the fabrication of gold nanorods with controlled faceted surfaces may be found in Zhang et al., Facet Control of Gold Nanorods, CS Nano, 2016, 10 (2), pp 2960-2974, which is incorporated herein by reference.

While FIGS. 1A-1D illustrate a variety of different types and configurations of magnetic nanostructures 10 it should be appreciated that still other shapes and configurations may be employed provided they exhibit ferromagnetic or superparamagnetic properties. Ferromagnetic properties refer to the ability of the magnetic nanostructure 10 to remain magnetized after removal of a magnetic field. Metals such as iron, nickel, or cobalt can be used in the magnetic nanostructures 10 and exhibit ferromagnetic properties. The superparamagnetic property refers to the property of magnetism which appears in small ferromagnetic particles such as nanoparticles where magnetization can randomly switch direction under the influence of temperature. These particles have no magnetic memory and do not retain any net magnetization once an external magnetic field has been removed.

As explained herein, the magnetic nanostructures 10 include, in one preferred embodiment, tips, ends, or surfaces that form a sharp tip or come to a point to aid in penetration of cell membranes or cell walls. In some embodiments, the magnetic nanostructure 10 has multiple layers. For example, with reference to FIG. 2, a base or substrate layer 40 may have a layer or coating 42 of a magnetically susceptible metal formed thereon. Such metals include by way of example, iron, nickel, and cobalt. A noble metal (e.g., gold) or metal oxide layer 44 may be deposited on or over the layer or coating 42. In some embodiments, one or more additional surface layers 46 (e.g., biocompatible surface layer 12) is formed over the noble metal or metal oxide layer. This may include a SAM formed on the noble metal layer 44 along with a linking layer such as polyethylenimine (PEI).

The biomolecular cargo 40 may include a molecule, multiple molecules, or higher order biological constructs. For example, molecules may include antigens, antibodies, proteins, protein fragments, enzymes, enzyme fragments, nucleic acids, and the like. Additionally, biomolecular cargo 40 may include, by way of illustration and not limitation, plasmids and/or targeted nucleases for gene-editing, e.g., CRISPR constructs such as guide RNA, Cas9 mRNA, and the like. One particular example of gene-editing molecules includes the CRISPR-Cas9 nuclease system that includes single-guide RNA (sgRNA) and the enzyme Cas9. The sgRNA directs the Cas9 nuclease to introduce sequence-specific targeted insertions, deletions, and genetic edits at specific genetic targets.

The individual magnetic nanostructures 10 may contain, in some embodiments, a single type of biomolecular cargo 40. In other embodiments, the individual magnetic nanostructures 10 may contain multiple types of biomolecular cargo 40. In some embodiments, a mixture of magnetic nanostructures 10 may be used with some magnetic nanostructures 10 carrying one (or more) types of biomolecular cargo 40 while other magnetic nanostructures 10 carry different biomolecular cargo 40.

The biomolecular cargo 40 may, in some embodiments, be electrostatically attached to the biocompatible surface layer 12 or additional surface layer 46. In other embodiments, the biomolecular cargo 40 may be covalently bound directly to the biocompatible layer 12 or additional surface layer 46. In some embodiments, one or more linker molecules may be used to attach the biomolecular cargo 40 to the magnetic nanostructures 10 (via covalent bond).

In one preferred embodiment, the magnetic nanostructures 10 include one or more sharp tips or pointed ends (e.g., 18, 20, 24, 32) as described herein that facilitate the introduction of the magnetic nanostructures 10 across the cell membrane or cell wall and into the interior of the cell 100. In this regard, according to one embodiment, the magnetic nanostructures 10 are needle-like or resemble a spear. Of course, it should be understood that a variety of shapes and configurations of magnetic nanostructures 10 are contemplated to fall within the scope of the invention including the specific shapes and configurations illustrated in FIGS. 1A-1D.

As described herein, the magnetic nanostructures 10 may be formed using various nanofabrication techniques known to those skilled in the art. Examples include nanosphere lithography, photolithography, soft lithography, etching, selective or seed growth, and oriented growth which can be used to fabricate the nanostructures contemplated herein. It may even be possible to grow magnetic nanostructures 10 by chemical or vapor deposition. Note that the underlying structure that forms the magnetic nanostructure 10 need not necessarily be magnetic; rather, nanostructures can be subsequently coated to be made magnetic (e.g., coated with a ferromagnetic or magnetically susceptible material such as nickel, iron, cobalt, or the like). A ferromagnetic or magnetically susceptible material may also be embedded within or deposited on the nanostructures. In one preferred embodiment, the magnetic nanostructures 10 are formed as magnetic nanospears 10 using nanosphere lithography. In nanosphere lithography such as that illustrated in FIGS. 5A-5D, spherical particles of polystyrene, silica, or other materials (e.g., with diameters ranging from about 200 nm to about 10 microns) serve as templates for underlying substrate patterning. FIG. 5A illustrates polystyrene (PS) beads that are formed on a silicon substrate. The diameters of the PS beads can be reduced using oxygen plasma etching and the underlying substrate etched away using (e.g., Reactive Ion Etching (RIE)). The substrate may include silicon, silicon dioxide, or other materials.

With reference to FIG. 5A, dry etching such as RIE is used to etch the underlying substrate (e.g., Si, $SiO_2$, or other materials) vertically by using the PS beads as a mask. The nanospear arrays that are obtained in this process are then coated with a magnetic film using a ferromagnetic or magnetically susceptible material (e.g., nickel, iron, iron oxide, cobalt, or other magnetic materials) as illustrated in FIG. 5A. As explained herein, in some embodiments the magnetic nanostructures 10 are ferromagnetic while in other embodiments, the magnetic nanostructures 10 exhibit superparamagnetic properties. These properties may be selectively obtained by the particular coating of material used for the magnetic nanostructures 10 and/or the shape, size, or geometry of the magnetic nanostructures 10.

The magnetic film or layer that is applied to the nanospear array may be followed, in some embodiments, and with an inert noble metal film (e.g., gold, platinum, or noble metals) or one or more metal oxide layers. The magnetic film enables the magnetic manipulation of the magnetic nanostructures 10, while the noble metal film (e.g., gold layer) protects the underlying magnetic film from oxidization and enables loading of biomolecular cargo 14 via existing chemical tethering approaches. For example, the biomolecular cargo 14 may be held to the magnetic nanostructure through attractive electrostatic forces.

Figure 5D:
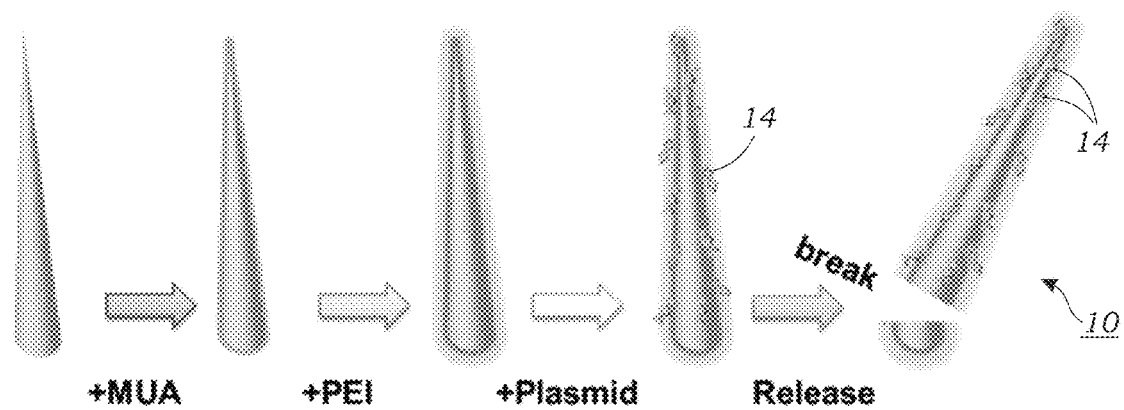
FIG. 5D schematically illustrates surface modification and release procedure of the Si/Ni/Au nanospears. 11-mercaptoundecanoic acid (MUA) is first coated on the Si/Au/Ni nanospears; next, polyethyleneimine (PEI) is electrostatically adsorbed as the second layer; negatively charged gene-modification cargo (e.g., DNA plasmid) is loaded onto the nanospear via physisorption. The functionalized Si/Ni/Au nanospears are finally released mechanically from the substrate and re-dispersed in deionized water.

Alternatively, the biomolecular cargo 14 may be held to the magnetic nanostructures using a covalent bond using a linker molecule that is functionalized on the surface of the magnetic nanostructures 10. For example, the magnetic nanostructures 10 may be coated with a gold surface layer 12 and thiol linkages may be used to form a self-assembled monolayer (SAMs) on the gold surface layer 12. One or more additional surface layers 46 may be used bind the biomolecular cargo 14 to the magnetic nanostructures 10. For example, FIG. 5D illustrates one embodiment wherein 11-mercaptoundecanoic acid (MUA) was used to form a SAM on the Au/Ni/Si magnetic nanospears 10 to make the surface negatively charged. Next, a second positively charged polyethylenimine (PEI) anchoring layer is deposited onto the magnetic nanospears 10 due to the electrostatic attraction. Then, negatively charged biomolecular cargo molecules 14 (e.g., plasmid with nucleic acid) can be tethered to this interface. After loading of the magnetic nanospears 10, the magnetic nanostructures or magnetic nanospears 10 are released from their substrate as illustrated in FIG. 5D by a mechanical breaking process (e.g., scraping, sonication, or other processes) and then dispersed in water, solution, or other fluid. While a covalent linkage is described above, dispersion forces such as van der Waals interactions can also be sufficient for this attachment. Nanoparticle carriers may also be used to adhere the biomolecular cargo 14 to the magnetic nanostructures Details regarding nanosphere lithography may be found in Xu et al., Multiple-Patterning Nanosphere Lithography for Fabricating Periodic Three-Dimensional Hierarchical Nanostructures, ACS Nano, 11(10), pp. 10384-10391 (2017), which is incorporated herein by reference. The magnetic nanospears 10 were designed and fabricated by nanosphere lithography using assembled PS particles as etch templates. Details are found in the Materials and Methods section found herein. Nanosphere lithography is an economical and scalable approach to generate large area periodic nanostructures such as holes, pillars, cones, needles, and wires on planer or curved substrates, which have been broadly applied in electronics, optics, energy conversion/storage, and biomedical studies. FIGS. 5A and 5D illustrate schematically the fabrication of magnetic nanostructures 10 in the form of magnetic nanospears 10. Generally, the monolayer of polystyrene PS spheres (2 µm in size) which self-organize into close-packed monolayers is assembled by slowly distributing an aqueous dispersion of the spheres drop cast onto a tilted glass slide. The monolayer is then transferred to a substrate (e.g., silicon) underneath the water/air interface by gently removing the liquid or drop casting. The array of spherical particles is then exposed to oxygen plasma to reduce the size of the spheres (e.g., to ~1.4 µm). Subsequently, reactive ion etching (RIE) is applied to etch the silicon substrate vertically with the PS spheres serving as a template. In this process, the PS spheres were also progressively etched while their sizes were reduced progressively to <50 nm. Thus, after the RIE has been applied to etch the silicon substrate vertically for a short distance, the PS spheres are subject to another oxygen plasma etching operation to reduce their size. This process is stopped and another round of RIE is performed to vertically etch the silicon substrate. This process produces a stair-step surface with layers having smaller and smaller sizes until the final RIE operation is performed. In some embodiments, only a single RIE operation is needed to form the needle or spear-like structures. Silicon nanospear arrays 48 are formed once the PS nanospheres are removed completely during the silicon etching process as seen in FIG. 5A.

Subsequently, nickel (Ni) and gold (Au) thin films are evaporated onto the nanospear arrays 48 at tilted angles to preserve the sharpness of final product Au/Ni/Si nanospears 10 as shown in FIG. 5A (see methods for details). The Ni thin film is ferromagnetic, endowing the nanospears 10 with magnetic properties; while the Au layer is both biocompatible and can be tailored readily for loading biomolecules, such as loading DNA, RNA, and proteins. In one embodiment, a layer-by-layer approach was used to place encapsulated nucleic acid molecules on Au/Ni/Si nanospears 10. In this embodiment, alkanethiol molecules can form structurally well-defined self-assembled monolayers (SAMs) on gold to offer wide synthetic flexibility to enable the conjugation of biomolecules to nanomaterials and engineered interfaces. In this embodiment, 11-mercaptoundecanoic acid (MUA) was used to form SAMs on the Au/Ni/Si nanospears 10 to make the surface negatively charged. Next, a second positively charged PEI anchoring layer is deposited onto the nanospears 10 due to the electrostatic attractions. Then, negatively charged biomolecular cargo molecules 14 (e.g., plasmids, DNA) can be tethered to this interface. In the experiments described herein, enhanced green fluorescent protein (eGFP)-expression plasmids were selected as the biomolecular cargo 14 to demonstrate the effectiveness of the magnetic nanospears 10. Finally, the MUA/PEI/eGFP-expression plasmids encapsulated magnetic nanospears 10 are carefully released from the Si substrate by gentle mechanical scraping and re-dispersed in deionized water or desirable media.

Figure 3A:
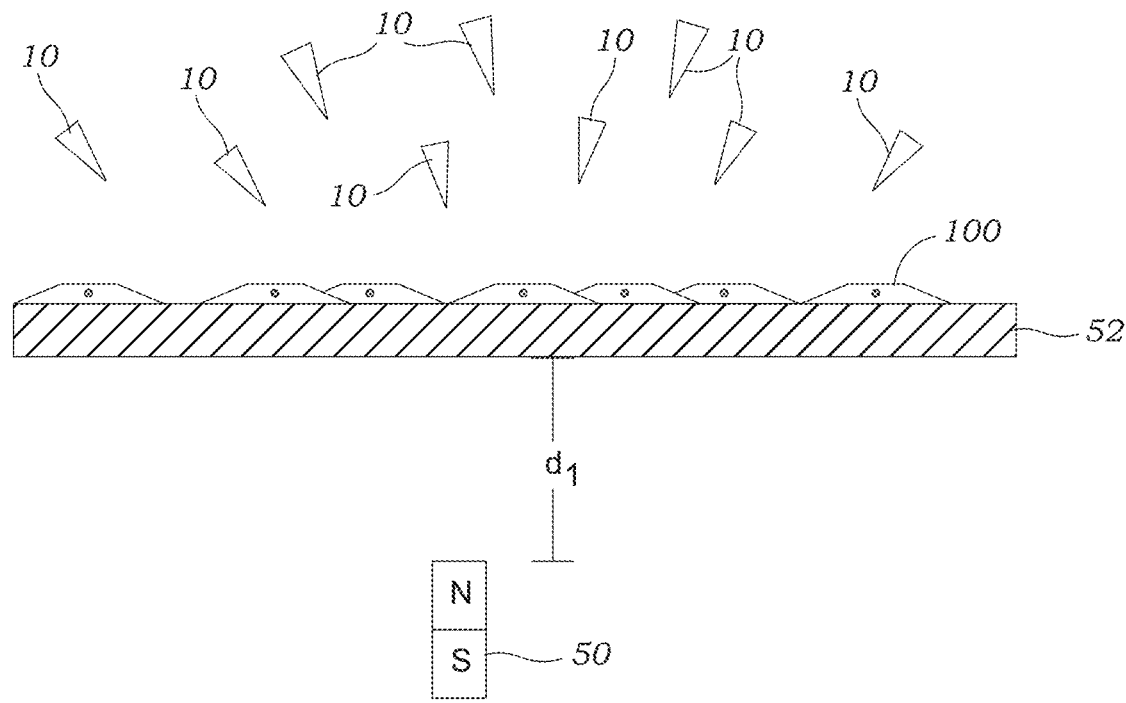
FIG. 3A illustrates one embodiment of magnetic nanostructures being oriented in response to the presence of a permanent magnet.
Figure 3B:
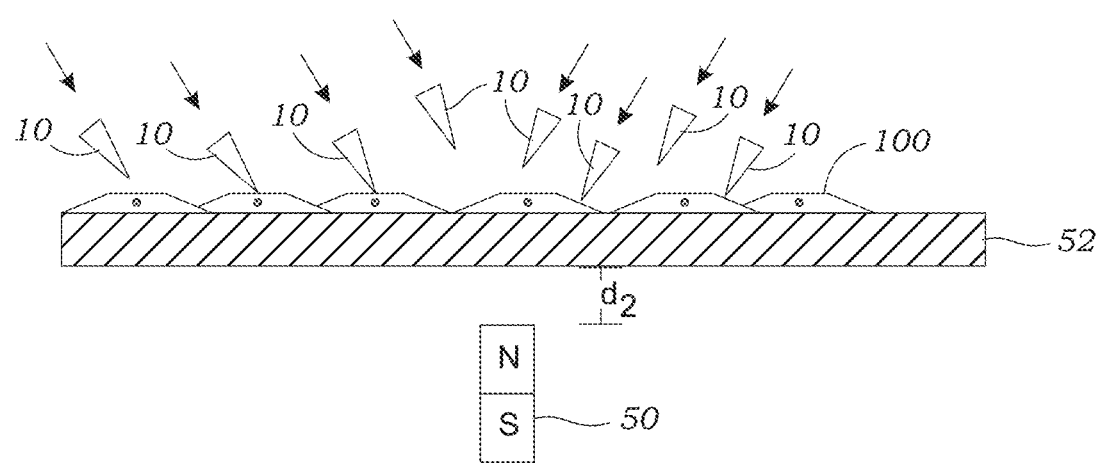
FIG. 3B illustrates the magnetic nanostructures of FIG. 3A being moved in response to the magnetic field of the permanent magnet to come into contact with the cells disposed on a substrate.
Figure 6A:
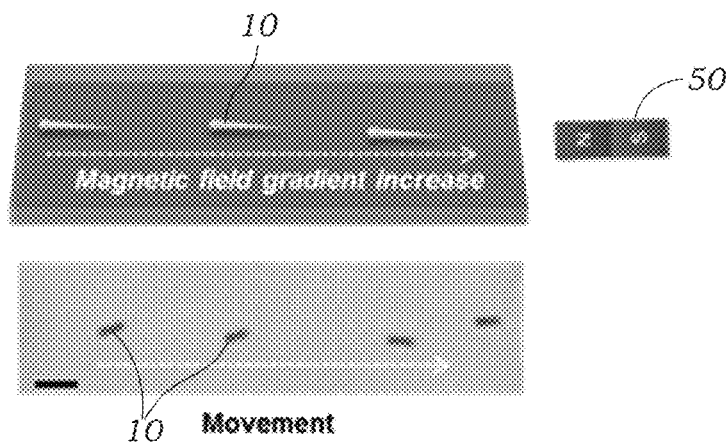
FIG. 6A schematically illustrates movement of magnetic nanospears using a magnet. Also illustrated is a photographic image (below) showing movement of a magnetic nanospear.
Figure 6B:
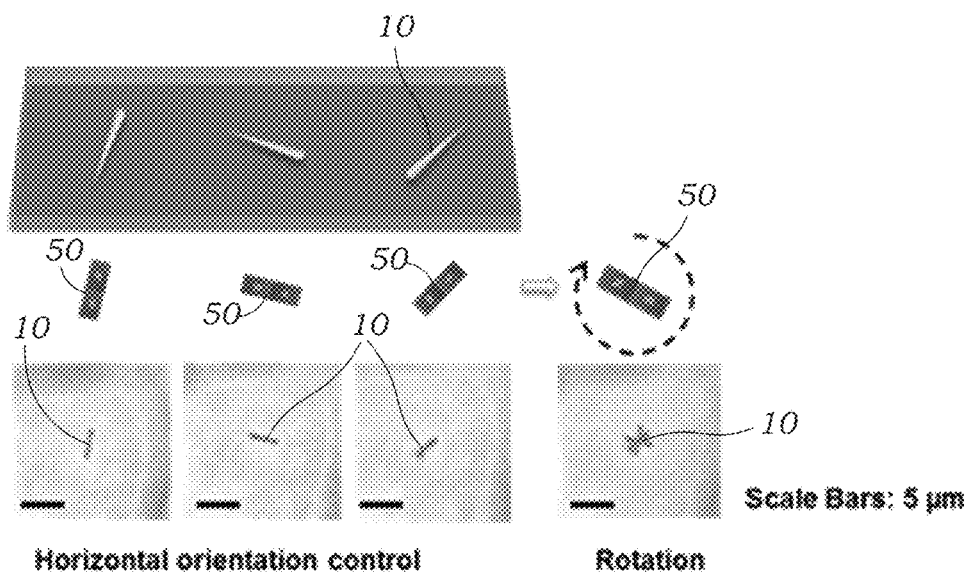
FIG. 6B schematically illustrates the manipulation of the orientation of magnetic nanospears in a horizontal plane. Also illustrated are photographic images showing horizontal orientation control using various orientations including rotation (by spinning the permanent magnet).

In one embodiment, the magnetic nanospears 10 dispersed in liquid can be readily manipulated by a nearby permanent magnet 50 such as a small neodymium-iron-boron disk magnet (of course, other permanent magnet materials or even electromagnets could also be employed). The physical orientation of each magnetic nanospear 10 can be aligned to the orientation of the magnet 50 to match their internal magnetization directions, due to the induced magnetic torque applied on the magnetic nanospear 10 by the magnetic field of the magnet 50. This is illustrated in FIGS. 3A, 6A, and 6B. This phenomenon is similar to a scenario frequently observed in everyday life where the direction of a compass aligns to the earth's magnetic field. Magnetic nanospears 10 can be directed to move toward the magnet 50 if the magnetic field gradient is large enough, i.e., they are in close proximity (FIGS. 3B and 6A). As a result, one can remotely manipulate the magnetic nanospears 10 to accomplish different tasks in fluid. The control of the direction, position, and rotation of a magnetic nanospear 10 in three-dimensional space is illustrated in FIGS. 3A and 6A-6C. The magnetic-field-induced movements of magnetic nanospears 10 are influenced by the magnetization of individual magnetic nanospears 10, which is defined by the mass of Ni (or other ferromagnetic material), the magnetization of the magnet 50, and the distance or separation between the two.

Figure 6C:
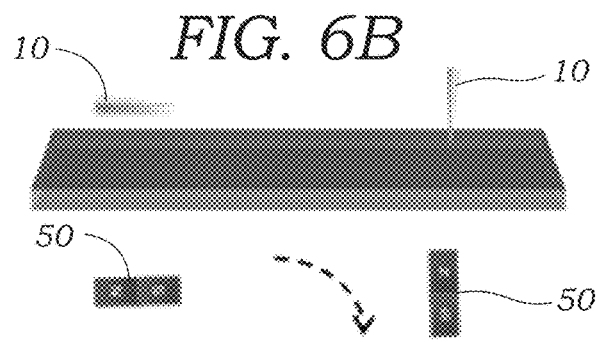
FIG. 6C schematically illustrates the manipulation of the orientation of magnetic nanospears in a vertical plane. Also illustrated are photographic images showing vertical orientation control so that the magnetic nanospear stands on end.
Figure 6C:
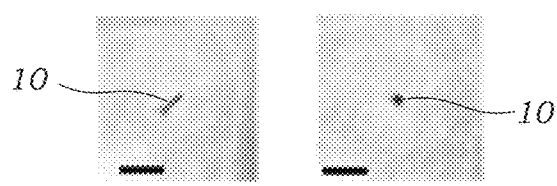

In some embodiments, the position, orientation, and speed of a magnetic nanospear 10 can be manipulated remotely by the applied external magnetic field gradient. When the magnet 50 is positioned near to the magnetic nanospears 10 (e.g., 2-20 cm or larger depending on the magnetic strength), the magnetic nanospears 10 align to the field of the magnet 50, enabling the direction of the magnetic nanospears 10 to be controlled in three dimensions. FIG. 3A illustrates this configuration where the magnetic nanospears 10 align to the magnetic field created by the magnet 50 located at a distance $d_1$ from the substrate 52 that holds the cells 100. When the magnet 50 is moved closer to the magnetic nanospears 10 (e.g., 0-2 cm or larger depending on the magnetic strength), the magnetic nanospears 10 move toward the magnet 50. This is illustrated in FIG. 3B where the magnetic nanospears 10 move (illustrated by arrows) toward the magnet that is now located a distance $d_2$ from substrate 52 carrying the cells 100. The speed of the magnetic nanospears 10 can be adjusted by carefully controlling the distance between the control magnet 50 and the magnetic nanospears 10 dispersed in solution, i.e., nanospears 10 move faster as the control magnet 50 is brought closer (~5 µm/sec). When the control magnet 50 is moved along a desired path while kept close to the magnetic nanospears 10 (e.g., 0-2 cm or larger depending on the magnetic strength), the magnetic nanospears 10 follow the control magnet 50, enabling precise directional control. Single or multiple magnetic nanospears 10 can be manipulated remotely and simultaneously in this way using a single control magnet 50. If the external magnet 50 is rotated horizontally or vertically, the magnetic nanospears 10 rotate exactly the same way, as illustrated in FIGS. 6B and 6C.

Figure 4:
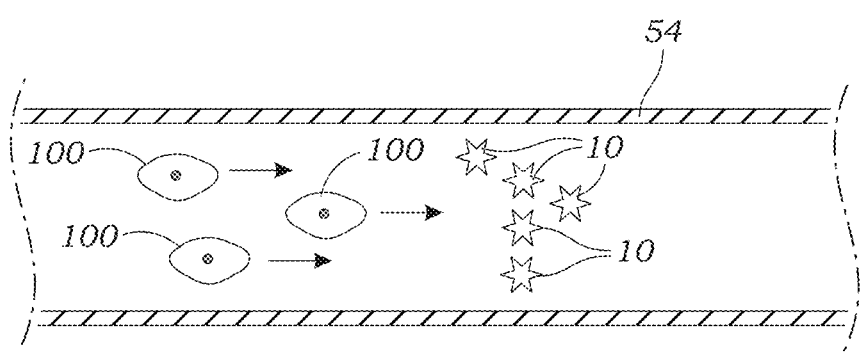
FIG. 4 illustrates another embodiment where cells flow in a microfluidic channel and come into contact with magnetic nanostructures.

In some embodiments such as those illustrated in FIGS. 3A, 3B, 8A, 9A the cells 100 are maintained stationary while the magnetic nanostructures 10 are moved toward the cells 100. For example, with reference to FIGS. 3A and 3B, the cells 100 may be located on a substrate 52. The substrate 52 may include a slide, well, channel, or chamber. In another embodiment such as that illustrated in FIG. 4, the magnetic nanostructures 10 are maintained in a substantially stationary state while the cells 100 move toward the magnetic nanostructures 10. In this embodiment, the magnetic nanostructures 10 may be held stationary within a microfluidic channel 54 while cells 100 that are contained in a fluid flow down the microfluidic channel 54 (in the direction of the arrows) and contact the magnetic nanostructures 10. The magnetic nanostructures 10 are maintained in a substantially stationary state by application of an external magnetic field. The magnetic nanostructures 10 may be held stationary within the actual fluid flow or, alternatively, the magnetic nanostructures 10 may be held stationary on one or more of the surfaces of the microfluidic channel 54 (e.g., the inner walls of the microfluidic channel 54). The microfluid channel 54 may be configured or designed to promote contact between the magnetic nanostructures 10 and the cells 100. In other embodiments, both the cells 100 and the magnetic nanostructures 10 may moving. For example, cells 100 may be contained in a flow or suspension while magnetic nanostructures 10 are moved to interact with the cells 100.

Figure 7A:
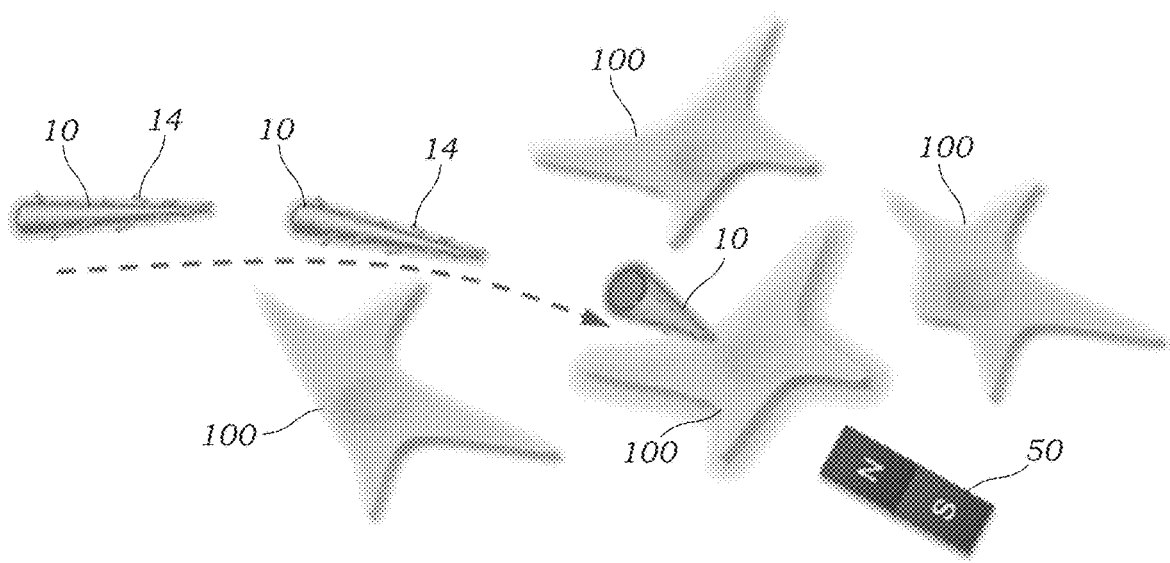
FIG. 7A illustrates a schematic illustration of enhanced green fluorescent protein (GFP)-expression plasmids modified Si/Ni/Au nanospear was transported and inserted into the target cell by a magnet to deliver the GFP-expression plasmid intracellularly.
Figure 7B:
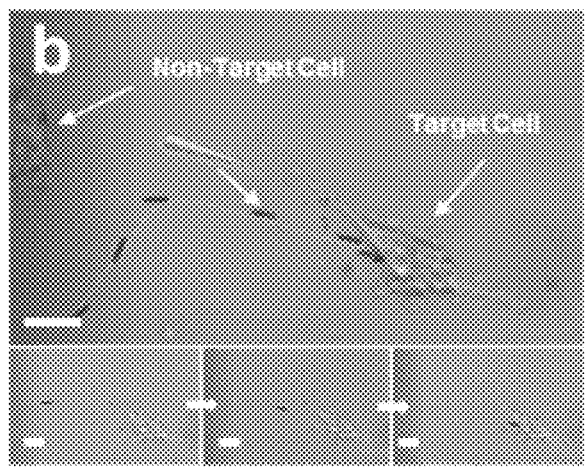
FIG. 7B illustrates overlaid optical images of the process of targeted intracellular delivery and control of trajectory of a single nanospear
Figure 7C:
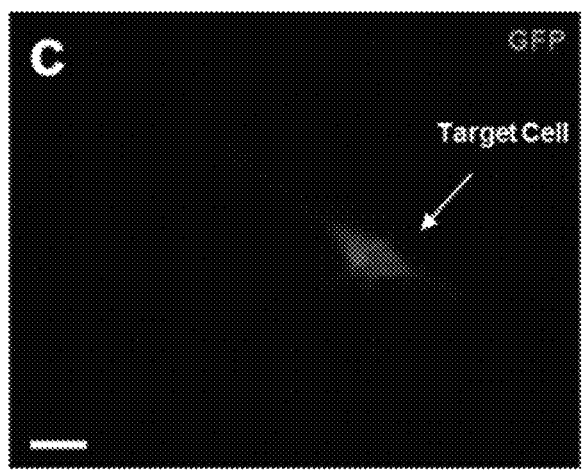
FIG. 7C illustrates a fluorescence microscopy image demonstrating the expression of GFP by a target U87 cell 24 h after transfection.
Figure 7D:
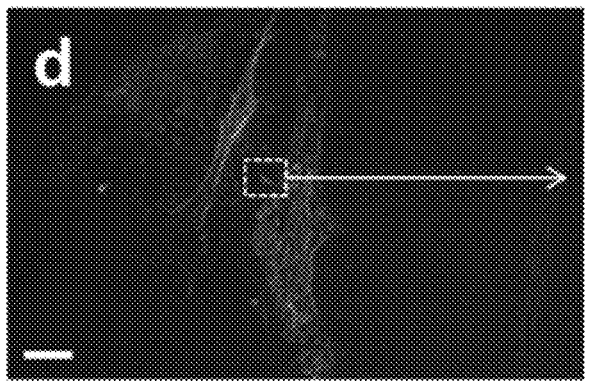
FIG. 7D illustrates a SEM image illustrating a nanospear docking with its target cell.
Figure 7E:
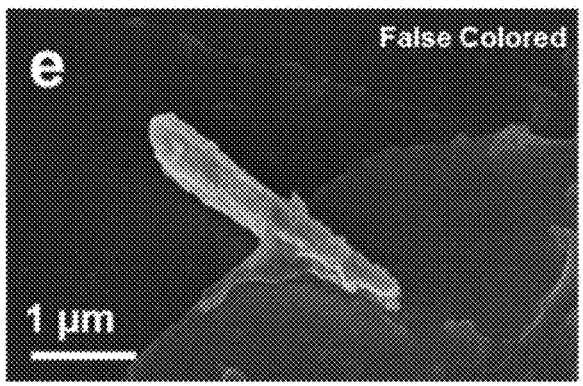
FIG. 7E illustrates a higher magnification SEM image. At higher magnification, the nanospear is observed to gently insert at the plasma membrane. The SEM image is false colored to visualize the magnetic nanospear and the cell. Unless noted, scale bars are 10 μm.

As previously explained, experiments were conducted whereby eGFP-expression plasmid (i.e., biomolecular cargo 14) was functionalized to the surface of magnetic nanospears 10 and manipulated by a magnetic field from a permanent magnet 50 to contact cells 100. The eGFP-expression plasmid functionalized magnetic Au/Ni/Si nanospears 10 were manipulated to move toward a target cell 100 and to penetrate its cell membrane gently, as illustrated in FIG. 7A. Overlaid optical images obtained from a video of a typical experiment are provided in FIGS. 7B-7E. After 24 h, fluorescence microscopy images indicate that the targeted cell 100 produces green fluorescence due to the successful transfection and expression of eGFP, while the non-target cells 100 remain unchanged. It appears from scanning electron microscopy (SEM) images that the tip of the magnetic nanospear 10 gently pierces the cell membrane in a manner akin to a splinter or an acupuncture needle (FIGS. 7D and 7E). It should be appreciated that the magnetic nanospears 10 are comprised of biocompatible materials, which are biodegraded by the target cells 100 over time.

Figure 8A:
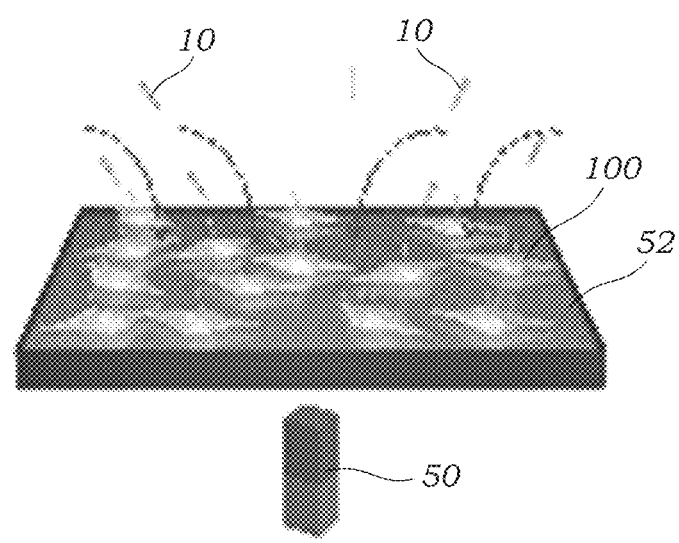
FIG. 8A is a schematic illustrating the manipulation of multiple magnetic nanospears to achieve high-throughput transfection.
Figure 8B:
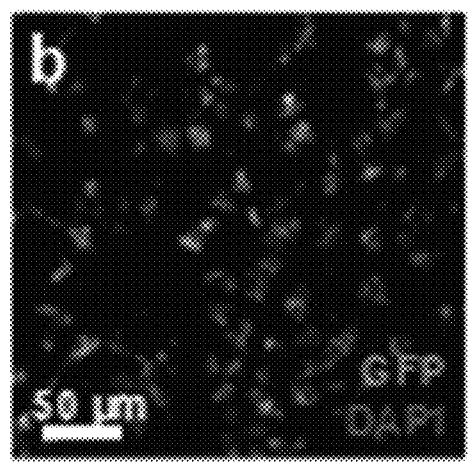
FIGS. 8B and 8C illustrate fluorescence microscopy images of target U87 cells 24 h post transfection by green fluorescent protein (GFP)-expression plasmid containing supramolecular nanoparticles tethered to nanospears. Green: GFP; Blue: 4',6-diamidino-2-phenylindole (DAPI).
Figure 8C:
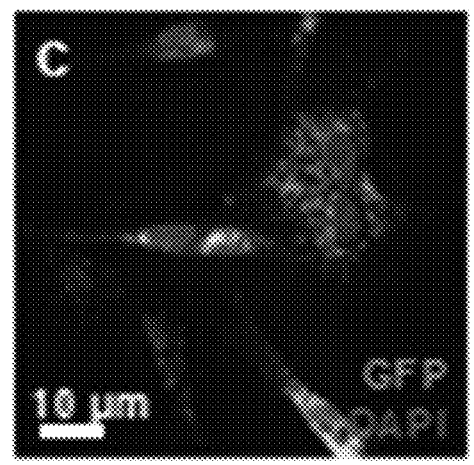
Figure 8D:
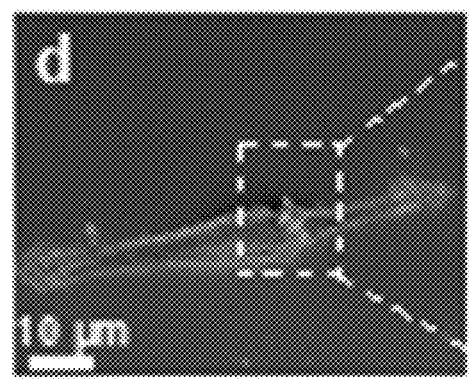
FIGS. 8D and 8E illustrate false colored scanning electron microscopy (SEM) images illustrating multiple magnetic nanospears inserting into a target cell.
Figure 8E:
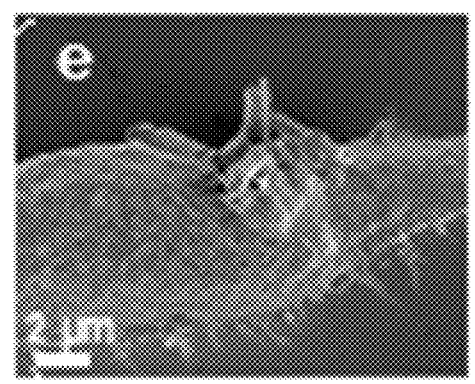
Figure 10A:
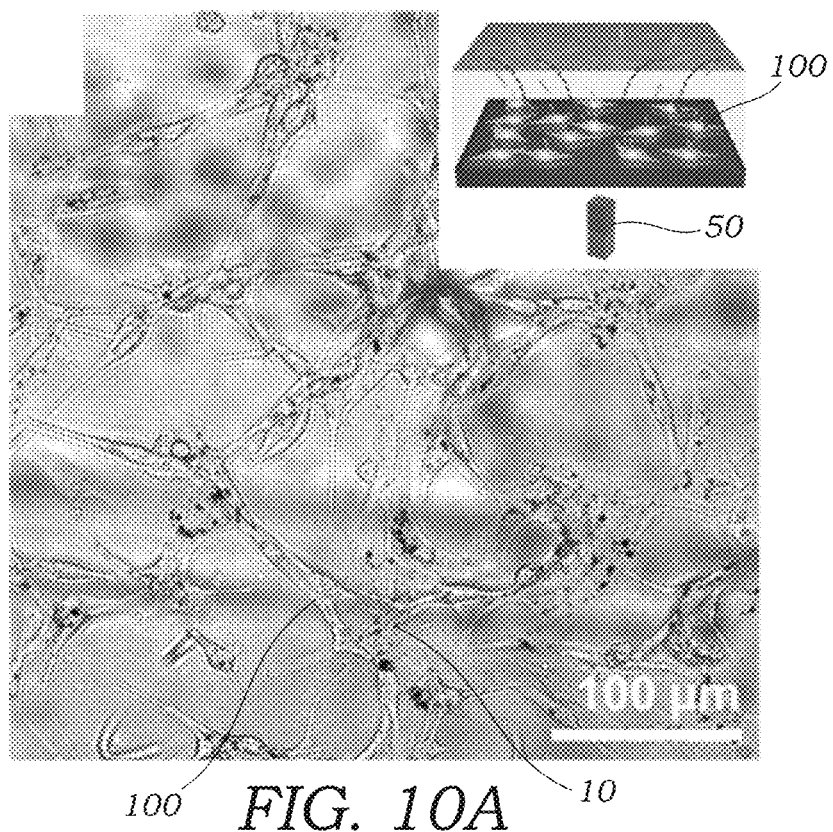
FIG. 10A illustrates a bright-field optical image that shows multiple nanospears docking on multiple cells.
Figure 10B:
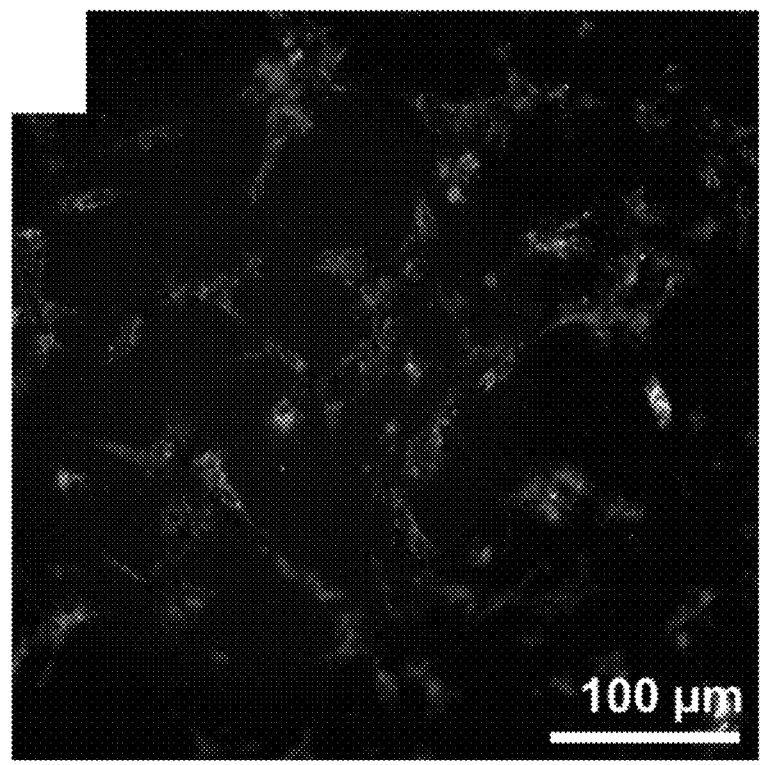
FIG. 10B illustrates a fluorescence microscopy image that, after 24 h incubation, demonstrates that a majority of the cells fluoresce in the green.

In another embodiment, a plurality of magnetic nanospears 10 can work cooperatively within a cell culture environment simultaneously to achieve robust transfection on a massive number of cells 100, as shown in the scheme and fluorescence microscopy images in FIGS. 8A-8E. In a typical experiment, ~1 million magnetic nanospears 10 dispersed in deionized water are added into a single well of a cell culture dish containing ~200,000 model U87 glioblastoma cells 100 (FIG. 8A). A magnet 50 is positioned concurrently along the backside the cell culture dish and moved slowly in either a clockwise or counterclockwise direction to guide the magnetic nanospears 10 as they travel and engage nearby cells 100, as shown in the bright-field optical image in FIG. 10A. The corresponding fluorescent image is seen in FIG. 10B that demonstrates that, after 24 h incubation, a majority of the cells fluoresce in the green. FIGS. 8B and 8C also illustrate fluorescence microscopy images of target U87 cells 24 h post transfection by green fluorescent protein (GFP)-expression plasmid containing supramolecular nanoparticles tethered to magnetic nanospears 10.

Figure 8F:
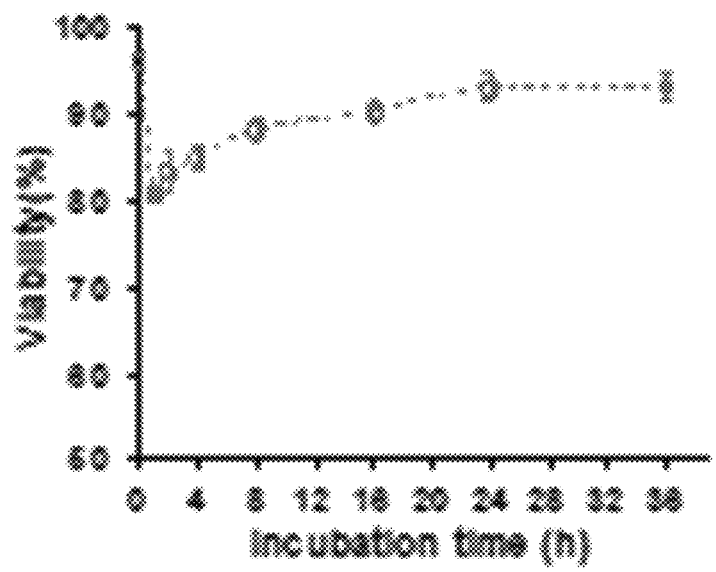
FIG. 8F is a graph illustrating cell viability test results show the initial viability post-transfection is >80%, and over time is noted to rise as a result of cell proliferation.

The control of these volleys of magnetic nanospears 10 can also be accomplished effectively by using a common magnetic stirring plate. Scanning electron micrographs of the target cells 100 after exposure to the magnetic nanospears 10 (FIGS. 8D and 8E) confirm that multiple magnetic nanospears 10 are able to dock at individual cells 100 by this approach. Taking advantage of this capability, the target cell population was transfected with bright eGFP expression to a high degree. Cell viability (FIG. 8F) was quantified after transfection via acridine orange/ethidium bromide staining assays. Viability tests of cells 100 transfected by the magnetic nanospears 10 show >90% survival with favorable proliferation potential relative to conventional methods.

Multiple magnetic nanospears 10 may also be applied for localized transfection/delivery, which is especially important for targeting specific populations of cells 100 in heterogeneous cultures or in vivo. Due to the availability of a variety of permanent magnets and reconfigurable electric magnets, one can tailor the effective size and strength of the external magnetic field applied at specific locations in order to manipulate multiple magnetic nanospears 10 for targeted transfection. This concept can be extended further to guide the trajectory of multiple magnetic nanospears 10 to treat cells 100 that are located at different locations on the same support substrate (e.g., cell culture dish). This strategy was demonstrated by guiding magnetic nanospears 10 carrying different expression plasmids sequentially to neighboring cells 100, as illustrated schematically in FIG. 9A. U87 cells were located at the left-hand portion of a substrate 52 (e.g., cell culture well) and magnetic nanospears 10 carrying eGFP-expression plasmid cargo 14 were selectively guided to this area (i.e., the left side of the substrate of FIG. 9A). After ~20 min, most of the magnetic nanospears 10 dock with their target cells 100 and are fixed at the cell membrane. The magnet 50 is then repositioned under the right-hand portion of the substrate 52 (i.e., cell culture dish) to deliver a red fluorescent protein (RFP)-expression plasmid to cells 100 that are located within this area. After 24 h, fluorescence microscopy images show cells on the left-hand side of the dish express green fluorescence (FIGS. 9B, 9D) while cells located on the right are red (FIGS. 9C, 9D). A 4',6-diamidino-2-phenylindole (DAPI) stain was used to highlight the nuclei of the cells. These experimental results demonstrate highly localized transfection as shown in FIGS. 9B and 9C. Note that the targeted positions are in close proximity in order to fit within the same field of view, which led to an observed transition region of fluorescence where cells 100 expressed both green and red fluorescence (FIG. 9D).

Thus, the magnetic nanostructures 10 may be targeted for delivery to a certain sub-population of cells 100 (e.g., those cells in a specific geographic region on a substrate 52 or even a single cell 100). For example, cells 100 of different phenotypes may be occupy or reside on different locations of a substrate 52. A user may manipulate and move the magnetic nanostructures 10 to target only a particular group or subset cells 100 (e.g., cells 100 of a particular phenotype).

Advances in molecular biology in the form of gene-editing tools are rapidly being leveraged in immunology and stem cell biology to drive innovative therapeutic approaches that utilize cells 100 as these "special forces" in the battle against a wide variety of diseases. The current non-viral vector-based methods used primarily to manufacture these extraordinary gene and cellular therapies unfortunately fall short at clinically relevant scales due, in part, to problematic toxicities and technical limitations resulting in low transfection efficiencies. Innovative solutions to address these challenges are approaching as nanotechnologies begin to close these gaps, enabling rapid, safe, and efficient delivery of biomolecular cargo to target cells and accelerating deployment of new medical interventions to the clinic.

The magnetic nanostructures 10 disclosed herein provide a simple, versatile, and effective platform for targeted intracellular gene delivery. A key feature is that the magnetic nanostructures 10 do not require a propellant for movement and positional control, avoiding potential toxicities that preclude their clinical use. While one focus described herein is the delivery of plasmid DNA, a variety of biomolecular cargo 14 are possible, enabling nanomedicine applications spanning molecular biology and with clinically viable products in sight. For example, the use of magnetic nanostructures 10 as described herein is compatible with good manufacturing practices and can be scaled easily for batch processing of large populations of cells 100, offering an elegant nanostructure-based solution to processing ex vivo harvested cells 100 and tissues for gene-modified transplantation applications. For example, volleys of magnetic nanospears 10 (or other nanostructures 10) can be assembled and directed to transfect large populations of cells (e.g., 1,000 to 10 billion or more cells 100). Further optimization of autonomous guidance capabilities will provide greater precision and open potential applications for in vivo cell 100 modification and gene marking. In an era where industries envision fleets of drones delivering packages to homes in the macroscopic world, guided magnetic nanostructures 10, such as magnetic nanospears 10, enable analogous solutions at the cellular level. These magnetic nanostructures 10 enable opportunities for interacting with cells 100 in new ways and offer an effective solution to circumvent existing barriers to gene modification at large scales for the generation of cell products for gene therapy.

Materials and Methods

Fabrication of nanospears: Nanosphere lithography employs periodic arrays of self-assembled close-packed monolayer nanospheres as templates to pattern underlying substrate materials. Polystyrene nanospheres (2 μm in diameter, Product No. 4202A, Thermo Fisher Scientific, MA, USA) were assembled into close-packed monolayers on a 2 cm×2 cm or larger Si substrate as reported, for example, in Haynes et al., Nanosphere Lithography: A Versatile Nanofabrication Tool for Studies of Size-Dependent Nanoparticle Optics. *J. Phys. Chem. B* 2001, 105, 5599-5611, which is incorporated herein by reference. Oxygen plasma (Oxford Plasmalab 80 Plus, Oxford Instruments, Abingdon, UK) with 35 sccm of $O_2$ and 10 sccm of Ar at a pressure of 60 mTorr and radio frequency (RF) power of 60 W for 10 min was applied to reduce the size of PS nanospheres to ~1.4 μm. To achieve sharp Si needles with high aspect ratios, a single-step RIE operation was performed on Si with the simultaneous flow of 20 sccm $C_4F_8$, 27 sccm $SF_6$, and 5 sccm Ar with inductively coupled plasma (ICP) power of 650 W for 7 mins (STS AOE Advanced Oxide Etcher). The $SF_6$ was used to etch the unprotected areas and the $C_4F_8$ was used to deposit fluorinated polymer to protect the side walls of the etched structures.

Fabrication of magnetic Au/Ni/Si nanospears: The nanospear substrates were loaded into the vacuum chamber of an electron beam metal evaporator (Kurt J. Lesker Company, Jefferson Hills, PA) and held at a base pressure of ~$1 \times 10^{-7}$ Torr. The substrates were mounted with fixed positions and orientations within the chamber such that their surface normal was inclined at an angle of 20° away from the metal source. A film of 100 nm Ni was deposited at rate of ~1 Å/s. Then, 40-nm Au films were deposited at an angle of 20° and −20° at rate of ~0.5 Å/s.

Surface modification of the magnetic Au/Ni/Si nanospears: A three-step layer-by-layer approach through electrostatic interaction is used to coat the Au/Ni/Si nanospears 10 with the desired biomolecular cargo. Step 1: The Au/Ni/Si nanospear substrate is immersed into a 11-mercaptoundecanoic acid solution (MUA, 1 mM in ethanol) for ~30 min to form MUA SAMs on Au/Ni/Si nanospears 10 via gold-thiolate bonds, then rinsed with ethanol and blow-dried with $N_2$ gas several times to remove excessive thiol molecules. Step 2: the substrate is immersed in 1 wt % poly(ethyleneimine) (PEI, Sigma Aldrich) solution for ~30 min, then washed with water. Step 3, the substrate is immersed in ~2 ml water with 2.0 μg of the desired expression plasmid and incubated overnight. Then, the substrate is rinsed in deionized water and dried. The plasmid-coated Au/Ni/Si magnetic nanospears 10 (~10 million) are carefully released from the Si substrate (0.5 cm²) by mechanical scraping with a razor blade, and then re-dispersed in ~2 ml water to reach a magnetic nanospear density of ~$5 \times 10^6$ ml$^{-1}$. Finally, ultrasound is used to reduce aggregation of the magnetic nanospears 10.

Targeted single cell intracellular gene delivery: For gene delivery to individual cells 100, the stock magnetic nanospear 10 solution is further diluted at least ~20−. U87 cells 100 are pre-cultured on a glass slide, which is mounted on the stage of an inverted optical microscope. In a typical experiment, 10 μl of diluted magnetic nanospear 10 solution is added to the cell culture medium. After ~1-2 min, magnetic nanospears 10 precipitate to the bottom of the cell culture medium. A cylindrical neodymium-iron-boron magnet 50 (diameter: 10 mm and length: 9 mm) with a magnetic field intensity of ~0.5 T measured from its surface is used to direct the mechanical motion of the magnetic nanospears 10 within the cell culture environment. The motion of individual magnetic nanospears 10 can be observed with an optical microscope (40×) as the magnet 50 is moved into proximity with the magnetic nanospears 10. When the magnet-nanospear separation is ~5 cm, the magnetic nanospears 10 align in the direction of the magnetic field. When the magnet is moved closer (<2 cm), the increased magnetic field gradient attracts the magnetic nanospears 10 to move toward the magnet 50, enabling control of both the direction and speed of motion of each magnetic nanospear 10. After docking a magnetic nanospear 10 to its target cell 100, the magnet 50 is held in position for ~5 min to ensure that the magnetic nanospear 10 is securely tethered to the cell 100. Expression of reporter fluorescent proteins from nanospear-treated cells 100 was monitored by fluorescence microscopy.

High-throughput intracellular gene delivery: A suspension containing ~1 million magnetic nanospears 10 carrying eGFP expression-plasmid cargo was added into a well of a 6-well disposable tissue culture plate containing ~200,000 U87 cells 100. A small magnet 50 was next positioned under the culture plate and moved back-and-forth for ~10 min to distribute the magnetic nanospears 10 throughout the entire cell culture area and to ensure that the magnetic nanospears 10 engage stably with the target cell population. Cells 100 treated with eGFP-nanospears 10 were monitored for fluorescence expression after 24 h.

While embodiments of the present invention have been shown and described, various modifications may be made without departing from the scope of the present invention. For example, while magnetic nanospears 10 are a focus of the experimental results it should be understood that other magnetic nanostructures 10 such as those disclosed in FIGS. 1B, 1C, and 1D may also be used. Moreover, the magnetic nanostructures 10 may also be used to target multicellular groups or cells or even tissue in some embodiments. In addition, while the magnet 50 is illustrated as a permanent magnet it should be appreciated that the external magnetic field may be applied by an electromagnet in alternative embodiments. The invention, therefore, should not be limited, except to the following claims, and their equivalents.

What is claimed is:

1. A method of transporting biomolecular cargo intracellularly into a plurality of cells comprising:
   providing a microfluidic channel;
   providing a plurality of magnetic nanostructures carrying the biomolecular cargo thereon within the microfluidic channel, wherein the plurality of magnetic nanostructures have at least one pointed end or tip;
   flowing a fluid containing the plurality of magnetic nanostructures within the microfluidic channel;
   applying an external magnetic field to maintain the plurality of magnetic nanostructures in a substantially stationary state along a width of the microfluidic channel and orients the plurality of magnetic nanostructures to place the at least one pointed end or tip of the plurality of magnetic nanostructures opposite to a direction of flow within the microfluidic channel; and
   flowing the plurality of cells within the microfluidic channel to physically contact the at least one pointed end or tip of the plurality of magnetic nanostructures.

2. The method of claim 1, wherein the plurality of magnetic nanostructures comprises a first type of magnetic nanostructure carrying a first biomolecular cargo thereon and a second type of magnetic nanostructure carrying a second biomolecular cargo thereon.

3. The method of claim 1, wherein the plurality of magnetic nanostructures are biodegradable by the plurality of cells.

4. The method of claim 1, wherein the plurality of magnetic nanostructures comprise a silicon base, followed by a nickel layer and a gold layer, followed by a layer of polyethyleneimine (PEI).

5. The method of claim 1, wherein the biomolecular cargo comprises one or more molecules.

6. The method of claim 1, wherein the biomolecular cargo comprises DNA-containing plasmids.

7. The method of claim 1, wherein the biomolecular cargo comprises targeted nucleases for gene editing and their associated guide nucleic acid sequences.

8. The method of claim 1, wherein the plurality of magnetic nanostructures comprise silicon coated with a magnetically susceptible metal followed by a noble metal or metal oxide layer.

9. The method of claim 8, wherein the biomolecular cargo is electrostatically and/or covalently attached or tethered to a deposited surface layer formed over the noble metal or metal oxide layer.

\* \* \* \* \*